US00PP19334P2

(12) United States Plant Patent
Nouws

(10) Patent No.: US PP19,334 P2
(45) Date of Patent: Oct. 14, 2008

(54) CHERRY LAUREL PLANT NAMED 'GAJO'

(50) Latin Name: *Prunus laurocerasus*
Varietal Denomination: Gajo

(76) Inventor: Wilhelmus Petrus Catharina Nouws, Pastoor van Vessemstraat 65, 4882 NJ Zundert (NL)

( * ) Notice: Subject to any disclaimer, the term of this patent is extended or adjusted under 35 U.S.C. 154(b) by 0 days.

(21) Appl. No.: 11/454,033

(22) Filed: Jun. 15, 2006

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV–ROM GTITM, Plant Variety Database, 2007/02, GTI Jouve Retrieval Sofware, Citation for Prunus 'Gajo' one page.*

Prunus laurocerasus 'Gajo' [online], [retrieval on Sep. 14, 2007]. Retrieved from the Internet at URL: http://www.van-liet–newplants.nl/plantinfo.php?id=72&lang=uk> one page.*

* cited by examiner

*Primary Examiner*—Kent L. Bell
*Assistant Examiner*—June Hwu
(74) *Attorney, Agent, or Firm*—C. A. Whealy

(57) ABSTRACT

A new and distinct cultivar of Cherry Laurel plant named 'Gajo', characterized by its compact, upright and somewhat outwardly spreading plant habit; freely branching habit; dense and bushy growth habit; relatively small and very dark green-colored leaves; and numerous small white-colored flowers.

2 Drawing Sheets

Botanical designation: *Prunus laurocerasus.*
Cultivar denomination: 'Gajo'.

BACKGROUND OF THE INVENTION

The present invention relates to a new and distinct cultivar of Cherry Laurel, botanically known as *Prunus laurocerasus* and hereinafter referred to by the name 'Gajo'.

The new Cherry Laurel is a naturally-occurring branch mutation of the *Prunus laurocerasus* cultivar Otto Luyken, not patented. The new Cherry Laurel was discovered and selected by the Inventor in a controlled outdoor nursery environment in Zundert, The Netherlands during the summer of 1996.

Asexual reproduction of the new Cherry Laurel by softwood cuttings in a controlled environment in Zundert, The Netherlands since 2003, has shown that the unique features of this new Cherry Laurel are stable and reproduced true to type in successive generations.

SUMMARY OF THE INVENTION

The cultivar Gajo has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Gajo'. These characteristics in combination distinguish 'Gajo' as a new and distinct cultivar of Cherry Laurel:

1. Compact, upright and somewhat outwardly spreading plant habit.
2. Freely branching habit; dense and bushy growth habit.

3. Relatively small and very dark green-colored leaves.
4. Numerous small white-colored flowers.

Plants of the new Cherry Laurel and the parent, the cultivar Otto Luyken, differ in the following characteristics:

1. Plants of the new Cherry Laurel are more compact and denser than plants of the cultivar Otto Luyken.
2. Plants of the new Cherry Laurel have smaller leaves than plants of the cultivar Otto Luyken.
3. Plants of the new Cherry Laurel have darker green-colored leaves than plants of the cultivar Otto Luyken.

Plants of the new Cherry Laurel can also be compared to plants of the cultivar Zabeliana, not patented. Plants of the new Cherry Laurel differ from plants of the cultivar Zabeliana in the following characteristics:

1. Plants of the new Cherry Laurel are more upright than plants of the cultivar Zabeliana.
2. Plants of the new Cherry Laurel have smaller leaves than plants of the cultivar Zabeliana.

BRIEF DESCRIPTION OF THE PHOTOGRAPHS

The accompanying colored photographs illustrate the overall appearance of the new Cherry Laurel, showing the colors as true as it is reasonably possible to obtain in colored reproductions of this type. Colors in the photographs may differ slightly from the color values cited in the detailed botanical description which accurately describe the colors of the new Cherry Laurel.

The photograph at the top of the first sheet comprises a side perspective view of a typical plant of 'Gajo' grown in an outdoor nursery.

The photograph at the bottom of the first sheet is a close-up view of a typical stem and leaves of 'Gajo'.

The photograph on the second sheet is a side perspective view of a typical flowering plant of 'Gajo'.

DETAILED BOTANICAL DESCRIPTION

The aforementioned photographs and following observations, measurements and values describe plants grown in Zundert, The Netherlands, under commercial practice in an outdoor nursery with day temperatures ranging from 2° C. to 12° C. and night temperatures ranging from −6° C. to 4° C. Plants were grown for about six years when the photographs and description were taken. In the following description, color references are made to The Royal Horticultural Society Colour Chart, 2001 Edition, except where general terms of ordinary dictionary significance are used.

Botanical classification: *Prunus laurocerasus* cultivar Gajo.

Parentage: Naturally-occurring branch mutation of the *Prunus laurocerasus* cultivar Otto Luyken, not patented.

Propagation:

*Type.*—By softwood cuttings.

*Time to initiate roots.*—About 50 days at 15° C.

*Root description.*—Fibrous, thick; white in color.

*Rooting habit.*—Moderate branching; medium density.

Plant description:

*Plant form/habit.*—Evergreen shrub. Compact, upright and somewhat outwardly spreading plant habit; inverted triangle. Freely basally branching habit; dense and bushy growth habit.

*Plant height.*—About 45.5 cm.

*Plant width (spread).*—About 39 cm.

*Lateral branches.*—Length: About 22.2 cm. Diameter: About 3.7 mm. Internode length: About 1 cm. Strength: Strong. Texture, developing: Smooth, glabrous. Texture, mature: Woody, rough. Color, developing: 138A to 143A. Color, mature: 197A.

Foliage description:

*Arrangement.*—Alternate, simple.

*Length.*—About 5.2 cm.

*Width.*—About 1.5 cm.

*Shape.*—Narrowly elliptic.

*Apex.*—Acute.

*Base.*—Attenuate.

*Margin.*—Entire; revolute; slightly undulate.

*Texture, upper and lower surfaces.*—Smooth, glabrous.

*Glands.*—Location: On lower leaf surfaces near the leaf base. Quantity: Two to four per leaf. Shape: Circular. Diameter: About 1 mm. Color: 146A.

*Venation pattern.*—Pinnate.

*Color, upper surface.*—139A; venation, 144B to 144C.

*Color, lower surface.*—146B to 146C; venation, 144B to 144C.

*Petiole.*—Length: About 6.5 mm. Diameter: About 1 mm. Texture, upper and lower surfaces: Smooth, glabrous. Color, upper and lower surfaces: 144B to 144C.

Flower description:

*Flower type/habit.*—Numerous single rotate flowers arranged on terminal and axillary racemes; flowers face outwardly to slightly upright. Racemes columnar in shape. Freely and uniformly flowering habit with about 64 flowers developing per inflorescence.

*Fragrance.*—Moderately fragrant; sweet.

*Natural flowering season.*—Continuously flowering during the spring in The Netherlands.

*Postproduction longevity.*—Flowers last about ten days on the plant. Flowers not persistent.

*Flower buds.*—Height: About 3 mm. Diameter: About 2.5 mm. Shape: Broadly ovate. Color: 155D.

*Inflorescence height.*—About 8.3 cm.

*Inflorescence diameter.*—About 2.4 cm.

*Flower diameter.*—About 8 mm.

*Flower depth.*—About 4 mm.

*Petals.*—Quantity per flower: Typically five in a single whorl. Length: About 3 mm. Lobe width: About 2.75 mm. Shape: Broadly ovate to orbicular. Apex: Rounded. Margin: Entire. Texture, upper and lower surfaces: Smooth, glabrous. Color: Developing petals, upper and lower surfaces: Close to 155D. Fully expanded petals, upper and lower surfaces: Close to 155D.

*Sepals.*—Quantity per flower: Typically five in a single whorl, fused towards the base; campanulate calyx. Length: About 2 mm. Width: About 1.5 mm. Shape: Ovate. Apex: Obtuse. Margin: Entire. Texture, upper and lower surfaces: Smooth, glabrous. Color, developing sepals, upper and lower surfaces: 144C. Color, fully expanded sepals, upper and lower surfaces: 144A to 144B.

*Peduncles.*—Length: About 7.8 cm. Diameter: About 2 mm. Angle: About 35° from vertical. Strength: Strong. Texture: Smooth, glabrous. Color: 144B to 144C.

*Pedicels.*—Length: About 2 mm. Diameter: About 1 mm. Angle: About 50° from vertical. Strength: Moderately strong. Texture: Smooth, glabrous. Color: 144C.

*Reproductive organs.*—Stamens: Quantity per flower: Typically twelve. Filament length: About 3 mm. Anther shape: Broadly oblong. Anther length: About 1 mm. Anther color: 158D. Pollen amount: Moderate. Pollen color: 158C to 158D. Pistils: Quantity per flower: One. Pistil length: About 3 mm. Stigma shape: Club-shaped. Stigma color: 151C to 151D. Style length: About 2.5 mm. Style color: 158D. Ovary color: 153C to 153D.

*Seed/fruit.*—Seed and fruit development have not been observed.

Disease/pest resistance: Plants of the new Cherry Laurel have not been noted to be resistant to pathogens and pests common to Cherry Laurel.

Garden performance: Plants of the new Cherry Laurel have been observed to have good garden performance and tolerate rain, wind, are winter-hardy to USDA Zone 5 and tolerate temperatures up to about 30° C.

It is claimed:

1. A new and distinct Cherry Laurel plant named 'Gajo' as illustrated and described.

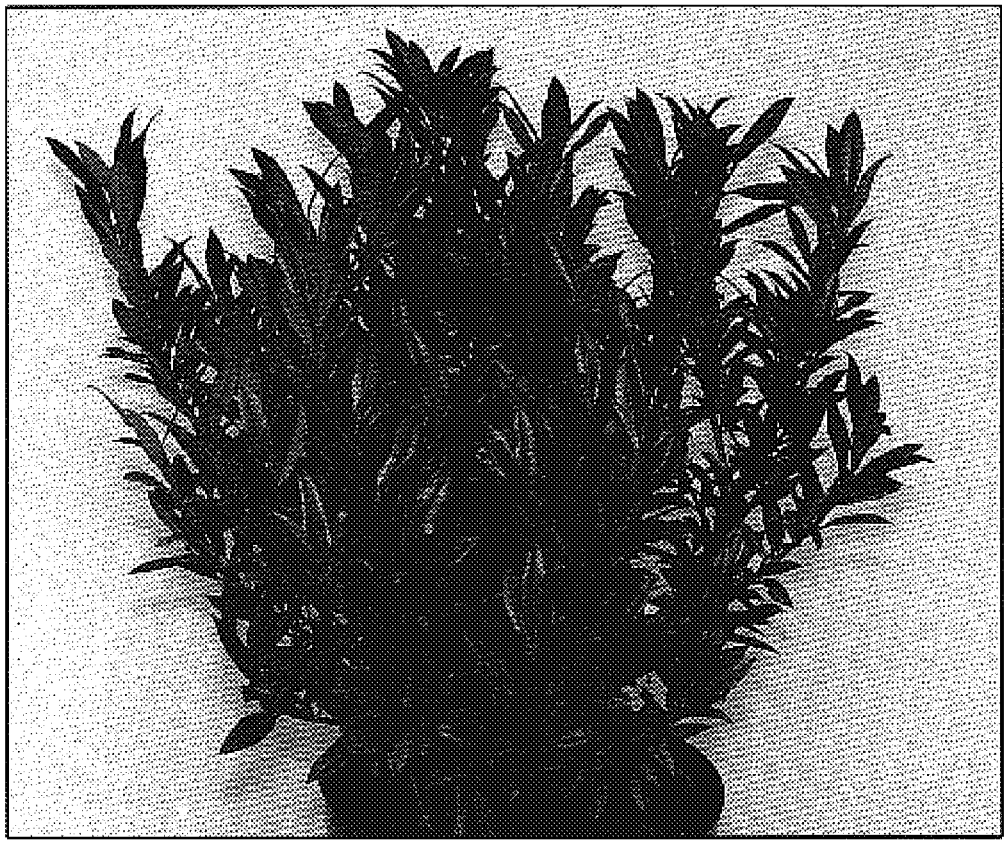
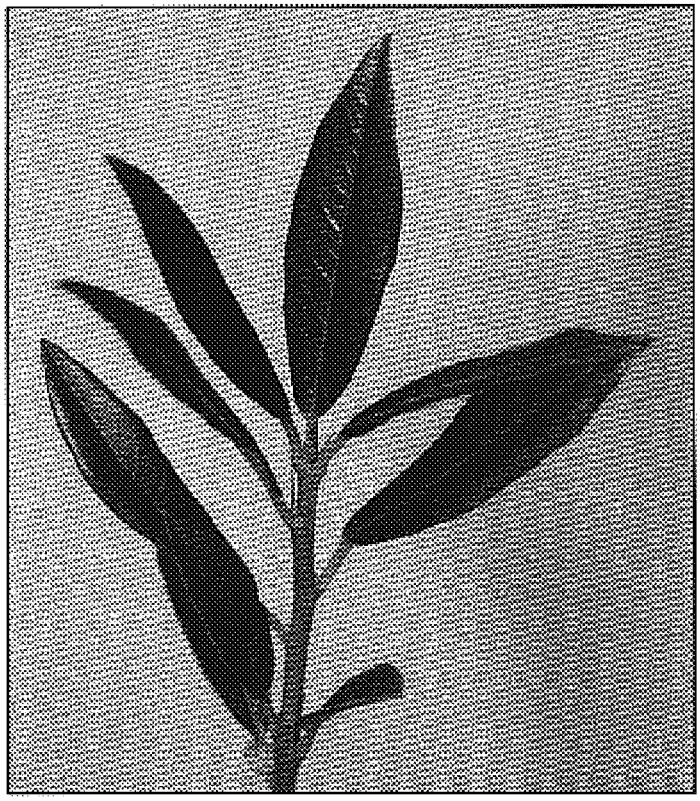

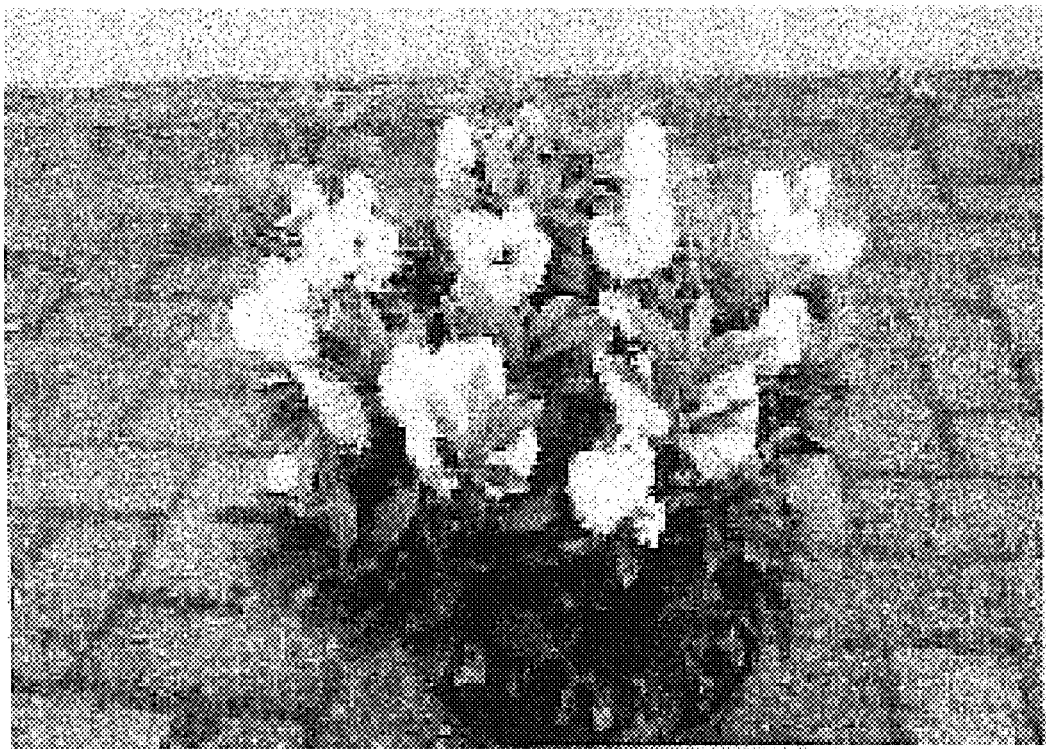

* * * * *